US007795276B2

(12) United States Patent
Bondy et al.

(10) Patent No.: US 7,795,276 B2
(45) Date of Patent: *Sep. 14, 2010

(54) IMIADAZO[4,5-C] PYRIDINE COMPOUND AND METHOD OF ANTIVIRAL TREATMENT

(75) Inventors: Steven S. Bondy, Danville, CA (US); David A. Oare, Belmont, CA (US); Winston C. Tse, San Mateo, CA (US)

(73) Assignees: Gilead Sciences, Inc., Foster City, CA (US); K.U. Leuven Research & Development, Leuven (BE); Gerhard Puerstinger, Igis (AT)

( * ) Notice: Subject to any disclaimer, the term of this patent is extended or adjusted under 35 U.S.C. 154(b) by 0 days.

This patent is subject to a terminal disclaimer.

(21) Appl. No.: 12/022,557

(22) Filed: Jan. 30, 2008

(65) Prior Publication Data
US 2008/0188516 A1    Aug. 7, 2008

Related U.S. Application Data

(63) Continuation of application No. 11/316,050, filed on Dec. 21, 2005, now abandoned.

(60) Provisional application No. 60/638,215, filed on Dec. 21, 2004.

(51) Int. Cl.
A61K 31/4353 (2006.01)
C07D 403/06 (2006.01)

(52) U.S. Cl. .................... 514/303; 546/118
(58) Field of Classification Search ................ 546/118; 514/303
See application file for complete search history.

(56) References Cited

U.S. PATENT DOCUMENTS

| 2,191,978 | A | 2/1940 | Balle et al. |
| 2,411,662 | A | 11/1946 | Martin et al. |
| 2,516,674 | A | 7/1950 | Havertown et al. |
| 2,548,863 | A | 4/1951 | Havertown et al. |
| 3,985,891 | A | 10/1976 | Kutter et al. |
| 4,358,387 | A | 11/1982 | Zoleski et al. |
| 4,565,816 | A | 1/1986 | Neumann |
| 4,692,443 | A | 9/1987 | Katner |
| 4,804,658 | A | 2/1989 | Manley et al. |
| 4,914,108 | A | 4/1990 | Khanna et al. |
| 4,988,707 | A | 1/1991 | Stealey et al. |
| 4,990,518 | A | 2/1991 | Khanna et al. |
| 5,011,832 | A | 4/1991 | Dininno et al. |
| 5,019,581 | A | 5/1991 | Khanna et al. |
| 5,057,517 | A | 10/1991 | Johnston et al. |
| 5,137,896 | A | 8/1992 | Van Daele |
| 5,208,242 | A | 5/1993 | Khanna et al. |
| 5,227,384 | A | 7/1993 | Khanna et al. |
| 5,302,601 | A | 4/1994 | Khannal et al. |
| 5,332,744 | A | 7/1994 | Chakravarty et al. |
| 5,374,638 | A | 12/1994 | Dhanoa et al. |
| 5,405,964 | A | 4/1995 | Mederski et al. |
| 5,438,063 | A | 8/1995 | Osswald et al. |
| 5,446,032 | A | 8/1995 | Whittaker et al. |
| 5,486,525 | A | 1/1996 | Summers, Jr. et al. |
| 5,585,492 | A | 12/1996 | Chandrakumar et al. |
| 5,587,372 | A | 12/1996 | Aszodi et al. |
| 5,607,944 | A | 3/1997 | Linz et al. |
| 5,719,306 | A | 2/1998 | Chandrakumar et al. |
| 5,723,492 | A | 3/1998 | Chandrakumar et al. |
| 5,854,265 | A | 12/1998 | Anthony |
| 5,859,035 | A | 1/1999 | Anthony et al. |
| 5,872,136 | A | 2/1999 | Anthony et al. |
| 5,874,452 | A | 2/1999 | Anthony |
| 5,880,140 | A | 3/1999 | Anthony |
| 5,883,105 | A | 3/1999 | Anthony |
| 5,939,557 | A | 8/1999 | Anthony et al. |
| 6,051,574 | A | 4/2000 | Anthony |
| 6,063,930 | A | 5/2000 | Dinsmore et al. |
| 6,080,870 | A | 6/2000 | Anthony et al. |
| 6,329,381 | B1 | 12/2001 | Kurimoto et al. |
| 6,376,515 | B2 | 4/2002 | Zhu et al. |
| 6,479,508 | B1 | 11/2002 | Beaulieu et al. |
| 6,492,384 | B1 | 12/2002 | Mederski et al. |
| 6,627,651 | B1 | 9/2003 | Shiraishi |
| 6,767,654 | B2 | 7/2004 | Tamao et al. |
| 6,770,666 | B2 | 8/2004 | Hashimoto et al. |
| 6,803,374 | B2 | 10/2004 | Priestley et al. |
| 6,835,739 | B2 | 12/2004 | Zhu et al. |
| 6,844,367 | B1 | 1/2005 | Zhu et al. |

(Continued)

FOREIGN PATENT DOCUMENTS

AU         643289         6/1991

(Continued)

OTHER PUBLICATIONS

Montgomery et al., 1-B-D-Arabinofuranosyl, etc., J. Med. Chem., 1982, 25, 96-98.*
Siddiqui et al., "3-Deaza- and, etc.," J. Med. Chem., 1995, 38, 1035-1038.*
Paeshuyse et al., "A Novel, Highly Selective, etc.," J of Virology, Jan. 2006, 80(1), 149-160.*
Vippagunta et al., "Crystalline Solid", Advanced Drug Delivery Reviews 48 (2001) 3-26.*
Gillory (in Brittain ed.), Polymorphism, etc., NY: Mercel Dekker, Inc., 1999, 1-2, 183-226.*
U.S. Appl. No. 11/658,625, filed Jul. 26, 2005, Kim et al.
U.S. Appl. No. 12/303,207, filed Feb. 12, 2008, Steven S. Bondy.
Akamatsu et al., "New Efficient Route for Solid-Phase Synthesis of Benzimidazole Derivatives," *J. Comb. Chem.* 4:475-483 (2002).

(Continued)

*Primary Examiner*—Patricia L Morris
(74) *Attorney, Agent, or Firm*—Clark & Elbing LLP

(57) ABSTRACT

The compound 5-((3-(2,4-trifluoromethyphenyl)isoxazol-5-yl)methyl)-2 -(2-fluorophenyl)-5H-imidazo[4,5-c]pyridine, together with the salts and solvates thereof. Also provided are compositions comprising this compound and pharmaceutically acceptable carriers, as well as the use of such compositions in the treatment or prophylaxis of viral infections.

4 Claims, No Drawings

U.S. PATENT DOCUMENTS

| | | | |
|---|---|---|---|
| 7,026,051 | B2 | 4/2006 | Schauer et al. |
| 7,098,231 | B2 | 8/2006 | Poupart et al. |
| 7,112,600 | B1 | 9/2006 | Hashimoto et al. |
| 7,223,785 | B2 | 5/2007 | Beaulieu et al. |
| 7,285,551 | B2 | 10/2007 | Hashimoto et al. |
| 7,294,457 | B2 | 11/2007 | Kukolj et al. |
| 2003/0073836 | A1 | 4/2003 | Priepke et al. |
| 2003/0108862 | A1 | 6/2003 | Kukolj et al. |
| 2004/0082635 | A1 | 4/2004 | Hashimoto et al. |
| 2004/0097438 | A1 | 5/2004 | Hashimoto et al. |
| 2004/0097574 | A1 | 5/2004 | Marshall |
| 2004/0171626 | A1 | 9/2004 | Beaulieu et al. |
| 2004/0186125 | A1 | 9/2004 | Poupart et al. |
| 2005/0026921 | A1 | 2/2005 | Eckhardt et al. |
| 2005/0096337 | A1 | 5/2005 | Ackermann et al. |
| 2005/0222198 | A1* | 10/2005 | Bondy et al. ................ 514/303 |
| 2005/0239821 | A1 | 10/2005 | Neyts et al. |
| 2006/0052602 | A1 | 3/2006 | Kim et al. |
| 2006/0229336 | A1 | 10/2006 | Kazmierski et al. |
| 2007/0021472 | A1 | 1/2007 | Zhu et al. |
| 2007/0032497 | A1 | 2/2007 | Hashimoto et al. |
| 2007/0244148 | A1* | 10/2007 | Bondy et al. ................ 514/303 |
| 2008/0199427 | A1 | 8/2008 | Bondy |
| 2009/0036460 | A1 | 2/2009 | Dowdy et al. |

FOREIGN PATENT DOCUMENTS

| | | |
|---|---|---|
| CA | 2093290 | 7/1993 |
| CA | 2158996 | 3/1994 |
| CA | 2357771 | 7/2000 |
| CA | 2471566 | 1/2003 |
| CA | 2423800 | 3/2003 |
| CA | 2496249 | 8/2003 |
| DE | 4211474 | 10/1993 |
| DE | 4230464 | 3/1994 |
| DE | 4236026 | 6/1994 |
| DE | 4309969 | 9/1994 |
| DE | 4318813 | 12/1994 |
| EP | 0076530 | 4/1983 |
| EP | 0138552 | 4/1985 |
| EP | 0228845 | 7/1987 |
| EP | 0232937 | 8/1987 |
| EP | 0300726 | 1/1989 |
| EP | 0344414 | 12/1989 |
| EP | 0417745 | 3/1991 |
| EP | 0462009 | 12/1991 |
| EP | 0510260 | 10/1992 |
| EP | 0605836 | 7/1994 |
| EP | 0706795 | 4/1996 |
| EP | 1132381 | 9/2001 |
| EP | 1162196 | 12/2001 |
| EP | 1386923 | 2/2004 |
| EP | 1400241 | 2/2004 |
| GB | 2158440 | 11/1985 |
| GB | 2264115 | 8/1993 |
| HU | 78019 | 5/1999 |
| IL | 89588 | 3/1989 |
| RU | 860463 | 5/1998 |
| SU | 813921 | 12/1986 |
| SU | 1048742 | 12/1986 |
| SU | 851940 | 4/1988 |
| WO | WO-92/22556 | 12/1992 |
| WO | WO-93/02080 | 2/1993 |
| WO | WO-93/14072 | 7/1993 |
| WO | WO-93/16075 | 8/1993 |
| WO | WO-94/12461 | 6/1994 |
| WO | WO-94/29321 | 12/1994 |
| WO | WO-95/02597 | 1/1995 |
| WO | WO-95/16687 | 6/1995 |
| WO | WO-96/11192 | 4/1996 |
| WO | WO-96/12703 | 5/1996 |
| WO | WO-96/15111 | 5/1996 |
| WO | WO-99/27929 | 6/1999 |
| WO | WO-00/20400 | 4/2000 |
| WO | WO-00/20416 | 4/2000 |
| WO | WO-00/20425 | 4/2000 |
| WO | WO-00/20445 | 4/2000 |
| WO | WO-00/39127 | 7/2000 |
| WO | WO-00/40583 | 7/2000 |
| WO | WO-00/40586 | 7/2000 |
| WO | WO-00/73307 | 12/2000 |
| WO | WO-01/60315 | 8/2001 |
| WO | WO-01/66526 | 9/2001 |
| WO | WO-01/85172 | 11/2001 |
| WO | WO-01/95910 | 12/2001 |
| WO | WO-02/04425 | 1/2002 |
| WO | WO-02/057425 | 7/2002 |
| WO | WO-02/067942 | 9/2002 |
| WO | WO-03/000254 | 1/2003 |
| WO | WO-03/004020 | 1/2003 |
| WO | WO-03/007945 | 1/2003 |
| WO | WO-03/010140 | 2/2003 |
| WO | WO 03/010141 | 2/2003 |
| WO | WO-03/014229 | 2/2003 |
| WO | WO-03/026587 | 4/2003 |
| WO | WO-03/057205 | 7/2003 |
| WO | WO-2004/005286 | 1/2004 |
| WO | WO-2004/018468 | 3/2004 |
| WO | WO-2004/019935 | 3/2004 |
| WO | WO-2004/033455 | 4/2004 |
| WO | WO-2004/043913 | 5/2004 |
| WO | WO-2004/054974 | 7/2004 |
| WO | WO-2004/067516 | 8/2004 |
| WO | WO-2004/072243 | 8/2004 |
| WO | WO-2005/063744 | 7/2005 |
| WO | WO-2006/029966 | 3/2006 |
| WO | WO-2006/033703 | 3/2006 |
| WO | WO-2006/069193 | 6/2006 |
| WO | WO-2008/005519 | 1/2008 |
| WO | WO-2009/009001 | 1/2009 |

OTHER PUBLICATIONS

Baba et al., "Synergistic Antiviral Effects of Antiherpes Compounds and Human Leukocyte Interferon on Varicella-Zoster Virus In Vitro," *Antimicrobial Agents Chemother.* 25:515-517, 1984.

Baginski et al., "Mechanism of Action of a Pestivirus Antiviral Compound," *Proc. Natl. Acad. Sci. U.S.A.* 97:7981-7986, 2000.

Barlin and Fenn, "A Carbon-13 Nuclear Magnetic Resonance Study of Protonation in Imidazo[4,5-c]pyridines," *Aust. J. Chem.* 34:1341-1344 (1981).

Barlin and Fenn, "The Preparation and 1H NMR Spectra of Some N-Methylpurines and Related Compounds," *Aust. J. Chem.* 36:633-638 (1983).

Barlin, "Ionisation Constants of Heterocyclic Substances, Part VIII. 1,3,5-Triazindenes," *J. Chem. Soc. B: Phys. Org.* 4:285-291, 1966.

Barraclough et al., "An Adventitious Synthesis of a 5-Methylimidazo[4,5-c]pyridine Derivative," *Tet. Lett.* 27:5997-6000 (1986).

Barraclough et al., "Inotropic "A" Ring Substituted Sulmazole and Isomazole Analogues," *J. Med. Chem.* 33:2231-2239 (1990).

Brown et al., "Purine Analogues as Amplifiers of Phleomycin. V. Thioethers of Several Heterocyclic Systems with One or Two Rings," *Aust. J. Chem.* 32:2713-2726 (1979).

Chou et al., "Quantitative Analysis of Dose-Effect Relationships: The Combined Effects of Multiple Drugs or Enzyme Inhibitors," *Adv. Enzyme Reg.* 22:27-55, 1984.

Cleve et al., "Derivate des Imidazo[4,5-b]- und Imidazo[4,5-c]-Pyridins," *Liebigs Ann. Chem.* 747:158-172, 1971 (and translation).

Curtin et al., "Discovery and Evaluation of a Series of 3-Acylindole Imidazopyridine Platelet-Activating Factor Antagonists," *J. Med. Chem.* 41:74-95 (1998).

Elion et al., "Antagonists of Nucleic Acid Derivatives. VIII. Synergism in Combinations of Biochemically Related Antimetabolites," *J. Biol. Chem.* 208:477-488, 1954.
Final Rejection, Dec. 16, 2008, U.S. Appl. No. 11/019,830.
Final Rejection, Mar. 19, 2007, U.S. Appl. No. 11/316,050.
Fletcher et al., "Heterocyclic Systems," *Nomenclature of Organic Adv. Ser.* pp. 49-64, 1974.
Grazul et al. Natural Product Letters (1994) 5(3):187-195.
Greenfield et al., "Increase in the Stability and Helical Content of Estrogen Receptor Alpha in the Presence of the Estrogen Response Element: Analysis by Circular Dichroism Spectroscopy," *Biochemistry* 40:6646-6652, 2001.
Griesser, Chapter 8, The Importance of Solvates (pp. 211-233), In the text, Polymorphism: In the Pharmaceutical Industry, Hilfiker, 2006.
International Preliminary Examination Report (PCT/BE03/00117) (mailed Sep. 3, 2004).
International Preliminary Report on Patentability for PCT/US2004/043112 dated Apr. 25, 2006.
International Preliminary Report on Patentability for PCT/US2005/026606 dated Feb. 20, 2007.
International Preliminary Report on Patentability for PCT/US2005/046477 dated Mar. 16, 2007.
International Preliminary Report on Patentability for PCT/US2007/015553 dated Jan. 13, 2009.
International Search Report for PCT/BE2003/000117 dated Dec. 16, 2003.
International Search Report for PCT/US2004/043112 dated Jun. 27, 2005.
International Search Report for PCT/US2005/026606 dated Feb. 13, 2006.
International Search Report for PCT/US2005/046477 dated Jun. 2, 2006.
International Search Report for PCT/US2007/015553 dated Mar. 6, 2008.
International Search Report for PCT/US2008/008259 dated Oct. 14, 2008.
Jacob III, P., "Resolution of (+/−) 5-Bromonornicotine. Sythesis of (R)- and (S)- Nornicotine of High Enantiomeric Purity," *J. Org. Chem.* 47:4165-4167, 1982.
Johnson, A.W. Invitation to Organic Chemistry 1999 Jones and Bartlett: Missisauga, Canada p. 24.
Jones, Maitland Organic Chemistry Norton: New York, 1997, p. 84-99.
Kariv et al., "Improvement of 'Hit-to-Lead' Optimization by Integration of In Vitro HTS Experimental Models for Early Determination of Pharmacokinetic Properties," *Comb. Chem. High Throughput Screen.* 5:459-472, 2002.
Kiyama et al., "Synthesis and Evaluation of Novel Nonpeptide Angiotesin II Receptor Antagonists: Imidazo[4,5-*c*]pyridine Derivatives with an Aromatic Substituent," *Chem. Pharm. Bull.* 43:450-460 (1995).
Kuno et al (1993) "Studies on Cerebral Protective Agents, IV. Synthesis of Novel 4-Arylpyridine and 4-arylpyridazine Derivatives with Anti-Anoxic Activity," Chem Phar. Bull. 41(1):156-162.
Lindenbach et al. (2005) "Unraveling Hepatitis C Virus Replication from Genome to Function," Nature 436-:933-938.
Lochmüller et al., "Chromatographic Resolution of Enantiomers Selective Review," *J. Chromatography* 113:283-302, 1975.

Mederski and Pachler, "Synthesis and Structural Assignment of Some N-Substituted Imidazopyridine Derivatives," *Tetrahedron* 48:10549-10558 (1992).
Non-Final Rejection, Dec. 12, 2008, U.S. Appl. No. 10/519,756.
Non-Final Rejection, Feb. 11, 2009, U.S. Appl. No. 10/583,814.
Non-Final Rejection, Mar. 12, 2008, U.S. Appl. No. 11/019,830.
Non-Final Rejection, Mar. 25, 2009, U.S. Appl. No. 12/022,557.
Non-Final Rejection, Oct. 29, 2008, U.S. Appl. No. 11/825,598.
Non-Final Rejection, Sep. 27, 2006, U.S. Appl. No. 11/316,050.
Okamoto et al., "Optical Resolution of Dihydropyridine Enantiomers by High-Performance Liquid Chromatography Using PhenylCarbamates of Polysaccharides as a Chiral Stationary Phase," *J. Chromatography* 513:375-378, 1990.
Penning et al., "Synthesis of Imidazopyridines as Potent Inhibitors of Leukotriene A4 Hydrolase," *Bioorg. Med. Chem. Lett.* 13:1137-1139, 2003.
Puerstinger et al. "Substituted 5-benzyl-2-phenyl-5H-imidazo[4,5-c]pyridines: A new class of pestivirus inhibitors" Bioorganic & Medicinal Chemistry Letters 2006, 16:5345-5349.
Puertstinger et al. "Antiviral 2,5-disubstituted imidazo[4,5-c]pyridines: From anti-pestivirus to anti-hepatitis C virus activity" Bioorganic & Medicinal Chemistry Letters 2007, 17:393-393.
Rigaudy et al., "Fundamental Heterocyclic Systems," *Nomenclature of Organic Adv. Ser.* pp. 53-76, 1979.
Robertson et al., "Structure-Activity Relationships of Arylimidazopyridine Cardiotonics: Discovery and Inotropic Activity of 2-[2-Methoxy-4-(methylsulfinyl)phenyl]-1*H*-imidazo[4,5-c]pyridine," *J. Med. Chem.* 28:717-727 (1985).
Savarino et al., "Spectral Behaviour of Linked Heterocyclic Systems and Related Dyes," *Spectrochim. Acta A: Mol. Biomol. Spectrosc.* 49A:1379-1393 (1993).
Self et al. (1991) "Romzarit: A Potential Disease-Modifying Antirheumatic Drug," J. Med. Chem. 34:772-777.
Stanovnik et al., "Methylation of Heterocyclic Compounds Containing NH, SH, and/or OH Groups by Means of N,N-Dimethylformamide Dimethyl Acetal," *Aust. J. Chem.* 34:1729-1738 (1981).
Vassilev et al., "Authentic and Chimeric Full-Length Genomic cDNA Clones of Bovine Viral Diarrhea Virus That Yield Infectious Transcripts," *J. Virol.* 71:471-478 (1997).
Wang et al., "Non-Nucleoside Analogue Inhibitors Bind to an Allosteric Site on HCV NS5B Polymerase. Crystal Structures and Mechanism of Inhibition," *J. Biol. Chem.* 278:9489-9495 (2003).
Written Opinion for PCT/US2004/043112 dated Oct. 18, 2005.
Written Opinion for PCT/US2005/046477 dated Jun. 2, 2006.
Written Opinion for PCT/US2007/015553 dated Jan. 7, 2009.
Written Opionion for PCT/US2005/026606 dated Feb. 13, 2006.
Yutilov et al., "Synthesis and Antiviral Activity of Spinaceamine," *Khim. Farm. Zh.* 23:56-59 (1989) (and translation).
Zhang, "Inhibitors of Hepatitis C—A Review of the Recent Patent Literature," *IDrugs* 5:154-158 (2002).
Zhang, "Studies on the Synthesis and Single Crystal Structure of 3-methyl-6-(p-methylphenyl) Pyridazine," 2001 Journal of Sichuan Normal University (Natural Science) 24(4):384-386 (and translation).

\* cited by examiner

IMIADAZO[4,5-C] PYRIDINE COMPOUND AND METHOD OF ANTIVIRAL TREATMENT

CROSS-REFERENCE TO RELATED APPLICATIONS

This application is a continuation of U.S. application Ser. No. 11/316,050, filed Dec. 21, 2005, now abandoned, which claims priority from U.S. Provisional Application No. 60/638,215, filed Dec. 21, 2004.

FIELD OF THE INVENTION

The present invention relates to compounds useful in the treatment or prophylaxis of viral infections, particularly those by the Flaviviridae and Picornaviridae families including hepatitis C virus (HCV).

BACKGROUND OF THE INVENTION

The Flaviviridae family consists of 3 genera, the pestiviruses, the flaviviruses and the hepaciviruses. It also contains the hepatitis G virus (HGV/GBV-C), which has not yet been assigned to a genus. Pestiviruses such as the Classical Swine Fever Virus (CSFV), the Bovine Viral Diarrhea Virus (BVDV) and the Border Disease Virus (BDV) cause infections of domestic livestock (respectively pigs, cattle and sheep) and are responsible for significant economic losses world-wide. BVDV, the prototypic representative of the pestivirus genus, is ubiquitous and causes a range of clinical manifestations, including abortion, teratogenesis, respiratory problems, chronic wasting disease, immune system dysfunction, and predisposition to secondary viral and bacterial infections.

Vaccines are used in some countries with varying degrees of success to control pestivirus disease. In other countries, animal culling and slaughter are used to contain pestivirus disease outbreaks.

The World Health Organization estimates that world-wide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1 to 5% of whom may develop liver cancer during the next ten years. The only treatment option available today is the use of interferon α-2 (or its pegylated from) either alone or combined with ribavirin. However, sustained response is only observed in about 40% of the patients and treatment is associated with serious adverse effects. There is thus an urgent need for potent and selective inhibitors of HCV.

The compound 3-[((2-dipropylamino)ethyl)thio]-5H-1,2,4-triazino[5,6-b]indole has been reported to selectively inhibit the replication of BVDV and other pestiviruses (Baginski S G et al., Proc. Natl. Acad. Sci. U.S.A. 2000 Jul. 5;97(14):7981-6). Currently, no pharmaceutical strategy is available for controlling pestivirus infections.

Coxsackie viruses belong to the enteroviruses of the Picornaviridae family. They cause a heterogeneous group of infections including herpangina, aseptic meningitis, a common-cold-like syndrome, a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis.

Currently only pleconaril (3-13,5-dimethyl-4-[[3-methyl-5-isoxazolyl)propyl]phenyl]-5-(trifluoromethyl-1,2,4-oxadiazole)) and enviroxime (2-amino-1-(isopropylsulfonyl)-6-benzimidazole phenyl ketone oxime) have been studied clinically for the treatment of infections with enteroviruses. Pleconaril is a so called "capsid function-inhibitor"; enviroxime prevents the formation of the RNA replicative intermediate. Enviroxime resulted in only modest clinical and virological benefit in some studies and no benefits in others. Clinical response with pleconaril has been observed in some studies, but the compound has not been approved by the Food and Drug Administration (hearing of Mar. 18, 2002).

Relevant disclosures include U.S. Pat. Nos. 4,914,108; 4,988,707; 4,990,518; 5,137,896; 5,208,242; 5,227,384; 5,302,601; 5,374,638; 5,405,964; 5,438,063; 5,486,525; 6,479,508; and U.S. Patent Publication No. US2003/0108862 A1, Canadian Patent No. 2423800 A1, German Patent Nos. 4211474 A1, 4236026, 4309969, 4318813, European Patent Nos. EP 0 138 552 A2, EP 0 706 795 A2, EP 1 132 381 A1, Great Britain Patent No. 2158440 A, PCT Patent Publication Nos. WO 00/20416, WO 00/39127, WO 00/40583, WO 03/007945 A1, WO 03/010140 A2, WO 03/010141 A2, WO 93/02080, WO 93/14072, WO 96/11192, WO 96/12703, WO 99/27929, PCT-US2004/43112, PCT-BE2003/000117, PCT-US2005/26606, Akamatsu, et al., "New Efficient Route for Solid-Phase Synthesis of Benzimidazole Derivatives", 4:475-483, *J. COMB CHEM.*, 2002, Cleve et al., "Derivate des Imidazo[4,5-b]-und Imidazo[4,5-c]pyridins", 747:158-171, *JUSTUS LIEBIGS ANNALEN DER CHEMACA*, 1971, Kiyama, et al., "Synthesis and Evaluation of Novel Nonpeptide Angiotensin II Receptor Antagonists: Imidazo[4,5-c]pyridine Derivatives with an Aromatic Substituent", 43(3):450-60, *CHEM PHARM BULL*, 1995, Medersk et al., "Synthesis and Structural Assignment of Some N-substituted Imidazopyridine Derivatives". 48(48):10549-58, *TETRAHEDRON*, 1992, Yutilov et al., 23(1):56-9, *KHIMIKO-FARMATSEVTICHESKII ZHURNAL*, 1989. The disclosures of all citations set forth herein are expressly incorporated by reference to the extent such disclosures are relevant to the contents herein.

A need exists for compounds having therapeutic properties, such as greater oral bioavailability, reduced toxicity, optimal clearance, increased potency and the like against viruses belonging to the family of Flaviviridae including hepatitis C virus, and against viruses belonging to the family of Picornaviridae. These and other objects of this invention will be apparent to one skilled in the art from consideration of this specification as a whole.

SUMMARY OF THE INVENTION

In accordance with the objects, the novel compound 5-((3-(2,4-trifluoromethyphenyl)isoxazol-5-yl)methyl)-2-(2-fluorophenyl)-5H-imidazo[4,5-c]pyridine

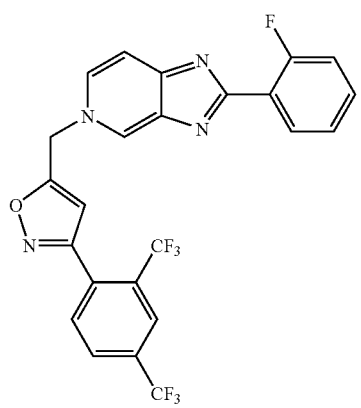

and its salts and solvates. Also provided are compositions comprising the compound of this invention together with pharmaceutically acceptable carriers, as well as the use of such compositions in the treatment or prophylaxis of viral, especially HCV, infections.

DETAILED DESCRIPTION OF THE INVENTION

The compound of this invention is employed for the treatment or prophylaxis of flaviviral or picornaviral infections, in particular HCV and BVDV.

The therapeutic compound of this invention is administered to a subject mammal (including a human) by any means well known in the art, i.e. orally, intranasally, subcutaneously, intramuscularly, intradermally, intravenously, intra-arterially, parenterally or by catheterization in a therapeutically effective amount, i.e., a flaviviral or picornaviral growth inhibiting amount or a flaviviral or picornaviral replication inhibiting amount. This amount is believed to be an amount that ensures a plasma level of between about 1 µg/ml and 100 mg/ml, optionally of 10 mg/ml. This optionally is achieved by administration of a dosage of in the range of 0.001 mg to 60 mg, preferably 0.01 mg to 10 mg, preferably about 0.5 mg to 1.5 mg per day per kg bodyweight for humans. Dosages of 1, 3, 6, 10, 20, 30 and 60 mg/kg are suitable for conducting toxicity studies in dogs and for extrapolating to suitable doses in humans. The optimal dosage of the compound of this invention will depend upon many factors known to the artisan, including bioavailability of the compound, its metabolism and distribution in the subject, its toxicity and its potency, among others. Proper dosing typically is determined in the preclinical and clinical settings, and is well within the skill of the ordinary artisan. The therapeutically effective amount of the compound of this invention optionally is divided into several sub-units per day or is administered daily or in more than one day intervals, depending upon the nature of the infection, the patient's general condition and the nature of the compound of this invention. Generally, the compound is administered daily.

The compound of this invention is employed in concert with other agents effective against Picornaviral or Flaviviral infections. Such agents include, for instance, interferon alpha, ribavirin, and/or compounds falling within the disclosures of EP1162196, WO 03/010141, WO 03/007945 WO 00/204425 and/or WO 03/010140 (and other filings within their patent families). Such other agents are used in conventional amounts, although if the efficacy of the compound of this invention and the other compound is additive then the amounts of each active agent optionally are commensurately reduced, and more so if the agents act synergistically. In general, however, the agents are used in their ordinary active amounts in the compositions.

Co-administered agents generally are formulated into unitary compositions with the compound of this invention so long as they are chemically compatible and are intended to be administered by the same route. If not, then they optionally are provided in the form of a medical kit or package containing the two agents in separate repositories or compartments.

The present invention further provides veterinary compositions comprising at least one compound of this invention together with a veterinary carrier therefor, for example in the treatment of BVDV. Veterinary carriers are materials useful for the purpose of administering the composition and are excipients which are otherwise inert or acceptable in the veterinary art and are compatible with the compound of this invention. These veterinary compositions are administered orally, parenterally or by any other desired route.

The compound of this invention is provided as the free base or as a salt. Salts typically are prepared by acid addition of certain organic and inorganic acids to the free base. Examples include (1) inorganic acids such as hydrohalogen acids, e.g. hydrochloric or hydrobromic acid, sulfuric acid, nitric acid, phosphoric acid and sulfamic acids; or (2) organic acids such as acetic, propanoic, hydroxyacetic, benzoic, 2-hydroxypropanoic, 2-oxopropanoic, lactic, fumaric, tartaric, pyruvic, maleic, malonic, malic, salicylic (e.g. 2-hydroxybenzoic), p-aminosalicylic, isethionic, lactobionic, succinic, oxalic and citric acids; organic sulfonic acids, such as methanesulfonic, ethanesulfonic, benzenesulfonic, p-toluenesulfonic, C1-C6 alkylsulfonic, benzenesulfonic, p-toluenesulfonic, and cyclohexanesulfamic acids. Also included within the scope of this invention are the salts of the compound of this invention with one or more amino acids, typically naturally-occuring amino acids such as one of the amino acids found in proteins. The acidic counterion desirably is physiologically innocuous and non-toxic or otherwise pharmaceutically acceptable, unless the salt is being used as an intermediate in preparation of the compounds whereupon toxicity is not relevant. While the free base is preferred, suitable salts include mesylate (methanesulfonic acid) and HCl.

The compound of this invention includes the solvates formed with the compound of this invention or their salts, such as for example hydrates, alcoholates and the like.

The compound of this invention optionally is formulated with conventional pharmaceutical carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose and stearic acid.

The term "pharmaceutically acceptable carrier" as used herein means any material or substance with which the active ingredient is formulated in order to facilitate its preparation and/or its application or dissemination to the site to be treated. Suitable pharmaceutical carriers for use in the compositions of this invention are well known to those skilled in the art. They include additives such as wetting agents, dispersing agents, adhesives, emulsifying agents, solvents, glidants, coatings, antibacterial and antifungal agents (for example phenol, sorbic acid, chlorobutanol), isotonic agents (such as sugars or sodium chloride), provided that the same are consistent with pharmaceutical practice, i.e. they are not toxic to mammals.

The pharmaceutical compositions of the present invention are prepared in any known manner, for instance by homogeneously mixing, coating and/or grinding the active ingredients in a one-step or multi-step procedure, with the selected carrier material and, where appropriate, other additives such as surface-active agents. Compositions containing the compound of this invention formulated into microspheres (usually having a diameter of about 1 to 10 gm) are useful as controlled or sustained release formulations.

Suitable surface-active agents, also known as emulgents or emulsifiers, are useful in the pharmaceutical compositions of the present invention. They are non-ionic, cationic and/or anionic materials having suitable emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl and oleyl) and, as further substituents, unsubstituted or halogenated lower alkyl, benzyl and/or hydroxy-lower alkyl radicals.

A more detailed description of surface-active agents suitable for this purpose is found in "McCutcheon's Detergents and Emulsifiers Annual" (MC Publishing Crop., Ridgewood, N.J., 1981), "Tensid-Taschenbucw", 2nd ed. (Hanser Verlag, Vienna, 1981) and "Encyclopaedia of Surfactants," (Chemical Publishing Co., New York, 1981).

The compound of this invention is administered by any route appropriate to the condition to be treated, such as oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient, but is generally oral.

Formulations of the compound of this invention for oral administration usually are presented as discrete units such as capsules, cachets or tablets each containing a predetermined amount of the active ingredient; as a powder or granular form; as a solution or suspension in an aqueous liquid or a non-aqueous liquid; or as an oil-in-water liquid emulsion or a water-in-oil liquid emulsion. The compound of this invention optionally is presented as a bolus, electuary or paste.

A tablet is made by compression or molding, optionally with one or more accessory ingredients. Compressed tablets are prepared by compressing in a suitable machine the compound of the invention in a free-flowing form such as a powder or granules, optionally mixed with a binder, lubricant, inert diluent, preservative, surface active and/or dispersing agent. Molded tablets typically are made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the compound is employed with a paraffinic or a water-miscible ointment base. Alternatively, the compound is formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention is constituted from known ingredients in a known manner. While this phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and *acacia*; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by aerosol or powder inhalers, of which numerous examples are available. Suitable formulations wherein the carrier is a liquid, for administration as for example a nasal spray or as nasal drops, include aqueous or oily solutions of the active ingredient Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations are presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compound of this invention is formulated into controlled release compositions in which the release of the compound is controlled and regulated to allow less frequency dosing or to improve the pharmacokinetic or toxicity profile of the invention compound. Controlled release compositions are prepared in accord with known methods, many of which involve formulating the active compound with one or more polymer carriers such a polyester, polyamino acid, polyvinyl pyrrolidone, ethylene-vinyl acetate copolymer, methylcellulose, carboxymethylcellulose and/or protamine sulfate. The rate of drug release and duration of action optionally is controlled by incorporating the active ingredient into particles, e.g. microcapsules, of a polymeric substance such as hydrogels, polylactic acid, hydroxymethylcellulose, polymethyl methacrylate and the other above-described polymers. Also suitable are colloid drug delivery systems such as liposomes, microspheres, microemulsions, nanoparticles, nanocapsules and so on. Depending on the route of administration, the pharmaceutical composition, e.g., tablets, may require protective coatings.

EXAMPLE 1

5-((3-(2,4-trifluoromethyphenyl)isoxazol-5-yl)methyl)-2-(2-fluorophenyl)-5H-imidazo [4,5-c] pyridine 2,4-(bis-trifluoromethyl)benzaldoxime To aromatic aldehyde (0.021 mol) suspended in EtOH/$H_2O$ (1:2, 230 mL, 0.09 M) was added hydroxylamine hydrochloride (1.58 g, 0.023 mol) and cooled to 4° C. To this solution was added aqueous NaOH 50% w/w (4.13 mL, 0.052 mol) dropwise. After stirring for 1.5 h at room temperature, the reaction mixture was acidified with 2N aqueous HCl and extracted with $CH_2C_4$ (3×50 mL). The organic solution was washed with saturated aqueous NaCl and dried over sodium sulfate. Removal of solvent gave crude oxime (5.3 g, quant.) that was used directly in the next step.

3-(2,4-(bis-trifluoromethyl)phenyl)-5-(chloromethyl) isoxazole 2,4-(bis-trifluoromethyl)benzaldoxime (9.75 g, 0.038 mol) was suspended in $CH_2C_2$ (45 mL, 0.85 M) and cooled to 4° C. Propargyl chloride (2.72 mL, 0.038 mol) was added to the reaction solution followed by dropwise addition of NaOCl (10-13% free chlorine, 37.6 mL, 0.061 mol). The reaction mixture was stirred at 4° C. for 15 min then heated to reflux for 3 h. After cooling to room temperature, the reaction was partitioned between $CH_2C_4$ and $H_2O$. The organic layer was separated, washed with saturated aqueous NaCl, and dried over sodium sulfate. After removal of solvent, the crude product chloromethylisoxazole was purified by column chromatography on silica (10% $CH_2Cl_2$/hexanes)(6.5 g ,0.020 mol).

5-((3-(2,4-trifluoromethyphenyl)isoxazol-5-yl)methyl)-2-(2-fluorophenyl)-5H-imidazo[4,5-c]pyridine To imidazopyridine (14.28 g, 0.067 mol) suspended in DMF (40 mL) was added aqueous NaOH 10% w/w (32.2 mL, 0.080 mol) dropwise followed by addition of the chloromethyl isoxazole from the previous step (26.3 g, 0.080 mol) in DMF (16 mL). After stirring for 12 h at room temperature, solvents were evaporated to give crude product as a tan solid. The crude solid was triturated with $H_2O$ (7×) and crystallized (2×) from MeOH/$H_2O$ (2:1) to provide pure title product.

NMR; 300 Mhz $D_6$MSO

Chemical shift, multiplicity, # of protons:

6.1,s,2
7.0,s,1
7.3, t, 2
7.4-7.5, m, 1
7.8-7.9, d, 1
7.9-8.0, d, 1
8.2-8.4, m, 4
9.2, s, 1

We claim:

1. 5((3-(2,4-trifluoromethyphenyl)isoxazol-5-yl)methyl) 2-(2-fluorophenyl)-5H-imidazo [4,5-c]pyridine, or a salt thereof.

2. A composition comprising the compound of claim 1 and at least one pharmaceutically acceptable carrier.

3. A method for treatment of an HCV infection comprising administering to a subject from 0.001 mg to 60 mg of a compound of claim 1.

4. The compound of claim 1 as the free base.

* * * * *